United States Patent
First et al.

(10) Patent No.: US 8,080,203 B2
(45) Date of Patent: *Dec. 20, 2011

(54) AIR STERILIZATION APPARATUS

(75) Inventors: Melvin W. First, Newton, MA (US);
Stephen N. Rudnick, Cambridge, MA (US); Richard L. Vincent, Bloomfield, NJ (US); Philip W. Brickner, Bronx, NY (US); John J. McEllen, Chagrin Falls, OH (US)

(73) Assignees: President and Fellows of Harvard College, Cambridge, MA (US); St. Vincent's Hospital and Medical Center of New York, New York, NY (US)

( * ) Notice: Subject to any disclaimer, the term of this patent is extended or adjusted under 35 U.S.C. 154(b) by 245 days.

This patent is subject to a terminal disclaimer.

(21) Appl. No.: 11/935,950

(22) Filed: Nov. 6, 2007

(65) Prior Publication Data
US 2009/0117000 A1    May 7, 2009

(51) Int. Cl.
*A61L 2/00* (2006.01)
*A62B 7/08* (2006.01)

(52) U.S. Cl. .................................. 422/24; 422/121

(58) Field of Classification Search .................. 422/24, 422/121
See application file for complete search history.

(56) References Cited

U.S. PATENT DOCUMENTS

| | | | |
|---|---|---|---|
| 2,398,627 A | 4/1946 | Disbro et al. | |
| 4,422,824 A * | 12/1983 | Eisenhardt, Jr. | 416/5 |
| 6,497,840 B1 | 12/2002 | Palestro et al. | |
| 6,855,295 B2 * | 2/2005 | Kulp | 422/121 |
| 6,884,399 B2 | 4/2005 | Reisfeld et al. | |
| 6,911,657 B2 | 6/2005 | Waluszko | |
| 7,763,212 B2 * | 7/2010 | McEllen | 422/121 |
| 2004/0047776 A1 | 3/2004 | Thomsen | |
| 2004/0175288 A1 * | 9/2004 | Horton, III | 422/4 |
| 2005/0058584 A1 | 3/2005 | Shyu | |
| 2005/0150386 A1 * | 7/2005 | Cheng | 96/223 |
| 2009/0004046 A1 * | 1/2009 | McEllen | 422/2 |

* cited by examiner

*Primary Examiner* — Walter D Griffin
*Assistant Examiner* — Christopher Vandeusen
(74) *Attorney, Agent, or Firm* — Kenyon & Kenyon LLP

(57) ABSTRACT

An air sterilization apparatus for sterilizing air that can include a fan assembly, which may be mounted in an upper-part of a room, and a UVC lamp to emit a UVGI field. The air sterilization apparatus may direct air across the UVGI field to sterilize the air. A baffle may also be provided to shield the eyes of occupants of the room from UVC energy contained in the UVGI field. The air sterilization apparatus may also include an illuminator lamp to provide illumination to a room.

9 Claims, 4 Drawing Sheets

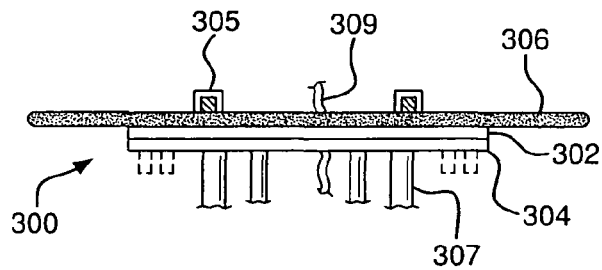
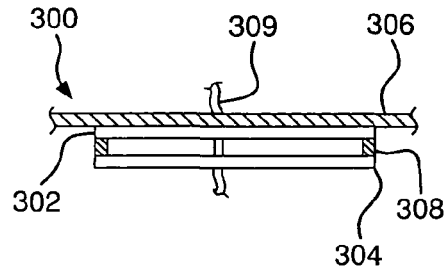
FIG. 3a        FIG. 3b
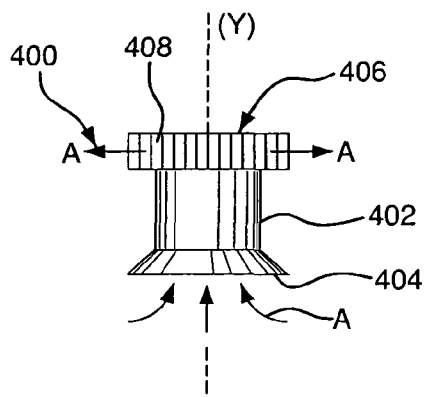
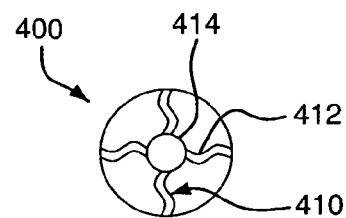
FIG. 4a        FIG. 4b
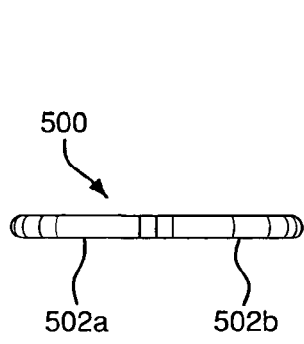
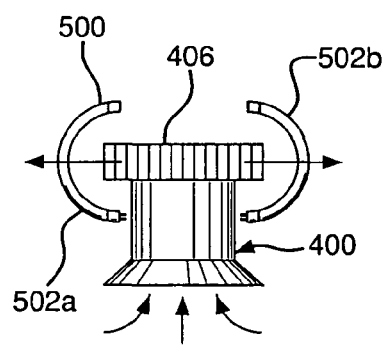
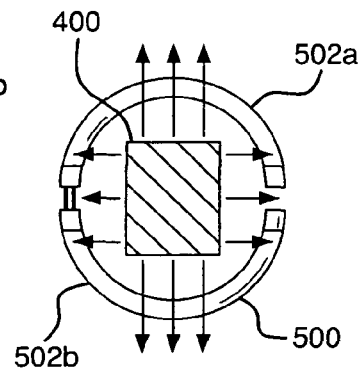
FIG. 5a        FIG. 5b        FIG. 5c

AIR STERILIZATION APPARATUS

TECHNICAL FIELD

The present application relates to air sterilization apparatuses and methods of their use. Certain embodiments of the present application relate to a louver-less air sterilization apparatus that is uniquely assembled to provide 360° of UVC irradiation and airflow to maximize UVC irradiance for the entire room in which it is installed. More particularly, germ-laden air can be first treated with intense radiation by passing air out of the apparatus across one or more novel UVC lamps. Then, the air is subject to prolonged UVC exposure as the air flows naturally across the ceiling within the UVC irradiation field.

BACKGROUND

As described in "Fundamental Factors Affecting Upper-Room Ultraviolet Germicidal Irradiation—Part I. Experimental," Journal of Occupational and Environmental Hygiene, 4:5, 321-331," (2007), the entire contents of which are hereby incorporated by reference, upper-room UVC may greatly lower the concentration of airborne organisms in the lower zone (e.g., below the irradiation field) of the room and thereby control the spread of airborne infection among occupants. Some of the factors determining the suitability of an air sterilization apparatus in clearing the lower air zone of infectious organisms are the quantity of UVC irradiance in the upper air zone, the rate of air mixing between the upper and lower air zones, the specific susceptibility of any particular microbe to UVC, and the control of eye exposure to UVC. See also "Fundamental Factors Affecting Upper-Room Ultraviolet Germicidal Irradiation—Part II. Predicting Effectiveness, " Journal of Occupational and Environmental Hygiene, 4: 352-362," (2007), the entire contents of which are hereby incorporated by reference.

To maintain these factors in balance, air sterilization systems using UVC irradiation must be carefully chosen to integrate luminaire selection, luminaire placement, and ventilation systems (e.g., air mixing). As can be seen in Table I of "Fundamental Factors Affecting Upper-Room Ultraviolet Germicidal Irradiation," many attempts have been made to balance these determinants. However, the currently-available air sterilization systems resulting from these attempts fall short, as they are inefficient in their production of UVC irradiation, ineffective in their exposure of room air to UVC, and/or overly expensive. For example, some existing devices are so shielded to avoid room occupant contact with UVC that their efficiency in exposing room air to UVC irradiation is excessively compromised.

Thus, a need exists to provide a more cost-effective, aesthetically pleasing, and improved air sterilization apparatus which can more effectively clear the lower air zone of infectious organisms, achieve the desired rate of air mixing, provide more effective and/or efficient exposure of room air to UVC and which avoids exposure of occupants of the room to UVC.

BRIEF DESCRIPTION

Certain embodiments of the present application can relate to a louver-less air sterilization apparatus that is uniquely assembled to provide 360° of UVC irradiation and airflow to maximize germ killing effectiveness for the entire room in which it is installed.

In accordance with certain embodiments of the present invention, a louver-less air sterilization apparatus may be provided that can include a fan assembly including a housing having an inlet and an outlet. The fan assembly may be adapted for mounting in an upper-part of a room and can include a UVC lamp to emit a ultraviolet germicidal irradiation (UVGI) field. The UVC lamp may be positioned proximate to the outlet of the fan assembly so that air is directed out of the outlet and across the UVGI field.

In other aspects, the present invention may include an air sterilization apparatus including a fan assembly having a fan and a housing. The housing can include an inlet for drawing air in and an outlet for directing air out. The fan assembly may be adapted for mounting in an upper-part of a room. The apparatus may also include at least one UVC lamp for emitting a UVGI field and the UVC lamp can be located proximate to the outlet of the fan assembly so that air is drawn into the fan assembly in a first substantially vertical direction and is directed out of the fan assembly in a second substantially horizontal direction across the upper-part of the room and through the UVGI field.

Other embodiments of the present invention can include a method of sterilizing air, including the steps of providing a fan assembly having an inlet and outlet to circulate air, emitting a UVGI field proximate to the outlet of the fan assembly, and drawing air in through the inlet in a first direction and directing air out through the outlet in a second direction across the UVGI field. Preferably, the air is first directed upward, then is directed in a substantially horizontal direction (e.g., a radial direction), thereby exposing air to UVGI as it travels out of the device.

In a preferred embodiment, the invention provides a generally round ceiling-mounted apparatus for air sterilization, in which the apparatus contains a fan assembly that pulls air up into the device in a first generally vertical direction and then directs the air in a second generally horizontal direction through a UVGI field. In a more preferred embodiment, the device would provide curved lamps that emit UVGI, and in a most preferred embodiment, the lamps are semicircular and are made of fused-quartz. It is also preferable that the apparatus is louver-less (e.g., does not include louvers); however, other arrangements using louvers can also be used.

The invention may be embodied by numerous other devices and methods. The description provided herein, when taken in conjunction with the annexed drawings, discloses examples of the invention. Other embodiments, which incorporate some or all steps as taught herein, are also possible.

BRIEF DESCRIPTION OF THE DRAWINGS

Referring to the drawings, which form a part of this disclosure:

FIGS. 3a-b show side views of bases which may be employed with the air sterilization apparatus of FIG. 1;

FIG. 4a shows a side view of a fan assembly of the air sterilization apparatus of FIG. 1;

FIG. 4b shows a bottom view of the fan assembly of FIG. 4a;

FIGS. 5a-c show UVC lamps which may used with the air sterilization apparatus of FIG. 1;

DETAILED DESCRIPTION

Figure 1:
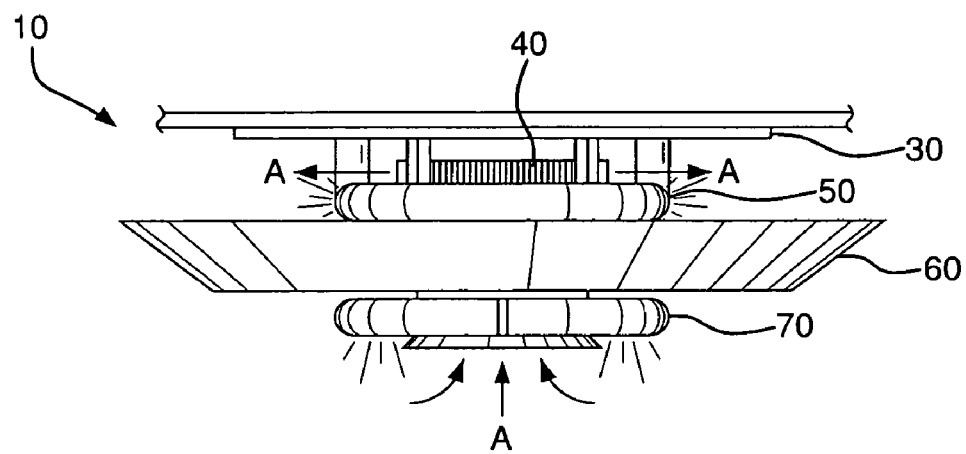
FIG. 1 shows a side view of an air sterilization apparatus as may be employed in accordance with certain embodiments of the present invention.
Figure 2:
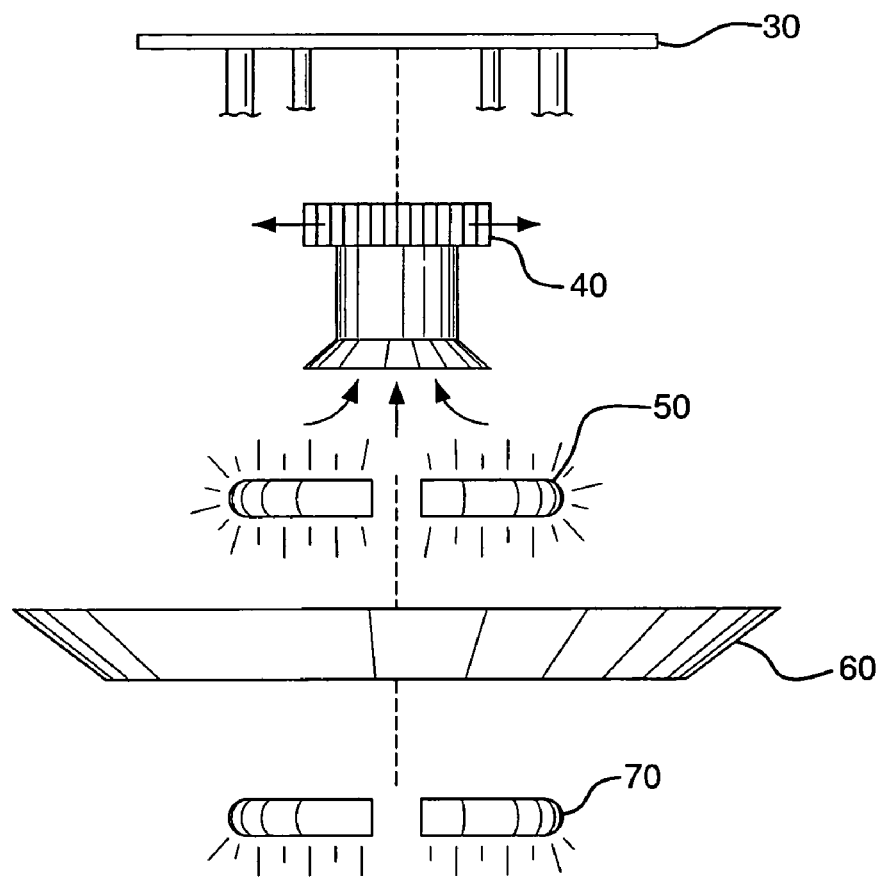
FIG. 2 shows an exploded view of the air sterilization apparatus of FIG. 1.

Referring initially to FIGS. 1-2, an air sterilization apparatus 10 is shown comprising a base 30, a fan assembly 40, a UVC lamp 50, a baffle 60, and an illuminator lamp 70. The components may be supported by any suitable means known in the art. For example, the base 30 may support some secondary components while these secondary components themselves can support yet other components.

As can be seen in the figures (air flow indicated by arrows), in a preferred embodiment, air (A) is drawn in through an inlet of the fan assembly 40 and out through an outlet of the fan assembly 40. In certain embodiments, fan assembly 40 may pull air from a lower-part of a room containing the apparatus to an upper-part of the room in a substantially vertical direction. The UVC lamp 50 emits an irradiation field (e.g., UVGI field) that can sterilize the air forced out of the fan assembly 40. The air is exposed directly to the UVC radiation, meaning that there are no louvers or other obstructions between the air to be sterilized or exposed to UVC radiation and the UV source. The baffle 60 can prevent UVC irradiation field emissions from directly and/or indirectly traveling below the baffle. Thus, the baffle can prevent or limit UV energy contained in the upper room UVC irradiation field from contacting and/or harming occupants of the lower part of a room where the air sterilization apparatus 10 is located. In addition, an illuminator 70 can be provided to illuminate the room. In the example of FIG. 1, a space(s) is shown between the base 30 and the baffle 60. Any sized space(s) may be used and the base 30 and/or baffle 60 may be adjustable in order to vary the distance between the components. In this embodiment, a larger space (s) is shown for illustrative (e.g., so interior components may be viewed). However, the space between baffle 60 and the ceiling can be important, as it allows adjustment of the length of time that air is exposed to UV energy as it travels horizontally just below the ceiling. In some settings increasing that distance will be important to increasing the effectiveness of the UVC irradiation while in other settings the need to limit lower room exposure to UVC may dictate that the space be narrowed.

FIGS. 3a-b show examples of bases 300 that may be employed in accordance with certain embodiments of the present invention.

The base of FIG. 3a is comprised of a mounting plate 302 and a cover 304. The mounting plate 302 may be secured to structural supports located in a target surface. In the example, the mounting plate 302 is attached to studs 305 located in the ceiling 306. It can be appreciated by one of ordinary skill in art that a variety of arrangements may be used for mounting the mounting plate 302 on a target surface. In addition, target surfaces may include, but are not limited to, ceilings, walls, floors, support members suspended from the ceiling, support members extending from the floor, etc.

In other embodiments, the base 300 may be adjustable to compensate for various target surfaces. For example, the base 300 can be adjustable so as to accommodate a range of ceiling heights.

As is seen in FIG. 3a, the base may include cover 304. The cover 304 may be designed to absorb UVC irradiation. Therefore, the cover 304 may be used to at least partially shield electrical components and/or wiring 309, which can run through the base 300, from the UVC irradiation field. A cover need not be provided. In other arrangements, the base itself may be made from a material designed to absorb and/or shield electrical components and/or wiring from UVC irradiation.

Some embodiments may also include concentric rings (shown as dashed lines in FIG. 3a) which extend from the cover 304 to prevent UVC irradiation from reflecting off the ceiling and into the lower portion of the room, for example, below the baffle 60 of FIGS. 1-2. If a cover is not used, the rings may extend directly from the mounting plate 302. Further, in other embodiments, anti-reflective and reflective coatings, paints, tapes, etc., may be used on various components to direct the UVC irradiation field as desired. In addition, the under surface of mounting plate 302 on cover 304 may be radiated by, for example, knurling or creating an "orange peel" surface to decrease reflectivity. Other types of surface modifications are known in the art.

FIG. 3a shows support members 307 extending from the cover 304. These support members 307 may be used for attaching components of the air sterilization apparatus thereto. Although supports are shown in this example, other arrangements well known in the art may be used. For example, a centrally disposed rod may extend through the components of the apparatus. The rod may be supported on one end by a stud in the ceiling and the other end can be configured to assist in supporting the components on the rod itself. In another embodiment, chains or cables can be utilized.

FIG. 3b shows an alternative arrangement for the base 300 that may be used in accordance with certain embodiments of the present invention. The base 300 of FIG. 3b may include a mounting plate 302 and a flange 308. In the example, the flange 308 extends downwardly from the mounting plate 302. As with FIG. 3a, a cover 304 may be positioned on the flange to shield electrical components and/or wiring 309 from UVC irradiation. Although the base 300 is ceiling 306 mounted in this example, the base may be mounted to any target surface.

FIG. 4a illustrates a fan assembly 400 that can be used in accordance with certain embodiments of the present invention. The fan assembly is comprised of a housing 402, an inlet 404, and an outlet 406. In the example, air (the path of which is indicated by A) is drawn into the housing 402 through the inlet 404 in a first direction and exits the housing 402 through the outlet 406 in a second direction. In this non-limiting example, the second direction is perpendicular to the first direction. In other words, the air is distributed from the outlet perpendicularly to and radially from a central axis (y) of the fan assembly, which in FIGS. 1-2, is parallel to a plane formed by the ceiling. Other airflow patterns may be used.

As shown in FIGS. 4a-b, the housing 402 is of generally annular shaped cross-section. The housing may also be shaped to facilitate air flow and/or positioning within the apparatus. For instance, as seen in FIG. 4a, the inlet 404 can be bell-shaped to facilitate air flow into the housing 402. Further, in the example, the outlet 406 portion of the housing 402 has a slightly larger diameter than the rest of the housing 402. The increased diameter of the outlet 406 may facilitate positioning of the housing 402 with respect to the UVC lamp. Other arrangements may be used.

In addition, the inner surfaces of the housing 402 may be baffled. For example, in a ceiling-mounted application, the inlet may be baffled to prevent UVC irradiation from exiting through the inlet 402 and into the room.

The outlet 406 of the housing 402 is provided with a plurality of slots 408 which extend 360° around the periphery of the housing 402; however, other arrangements for the outlet may be used. Thus, in accordance with certain embodiments of the present invention, air may exit the housing 402 radially over 360° (FIGS. 4a and 5b). Likewise, if the fan assembly were another shape, such as square shaped (FIG. 5c), air can also exit from around the entire periphery of the housing 402.

As seen in FIG. 4b, a centrifugal-type fan may be used. In the example, the centrifugal-type fan includes an impeller 410, that is located in the inlet of the housing, with a plurality of fan blades 412 located about a central shaft 414. A squirrel cage impeller may be used, such as wherein the central shaft is hollow and the axial blades extend around the periphery of the central shaft. In the example, as the impeller 410 rotates, air is drawn into the housing 402 through the inlet 404. The housing may also be shaped as desired to direct air flow.

Although a centrifugal-type fan is shown in the example of FIG. 4b, any suitable fan may be used, depending upon desired outputs. For example, fan assemblies providing airflows of 100-250 cfm may be suitable. For example, a variety of fans (axial, cross flow, etc.) may be chosen, based upon desired operating parameters (e.g., pressure, volume, noise, etc.).

The fan also includes an electric motor (not shown). The motor may be any conventional device that converts electrical energy into mechanical energy. The motor may be directly attached to an output shaft of the motor. The motor may be located within and/or outside of the housing. Both AC and DC motors may be used.

The fan assembly may be controlled remotely and/or have a switch on the assembly itself.

FIGS. 5a-c show UVC lamps configured to provide a generally uniform UVC irradiation field. Airflow and UVC intensity may be highest at the center of the apparatus and can decline as the distance from the center increases. This can enable maintenance of a generally uniform irradiation field.

Any number of UVC lamps of diverse sizes and shapes (e.g., linear, circular, curved, semi-circular, U-shaped, etc.) may be used. For example, in FIG. 5a, two horizontally arranged semi-circular UVC lamps (502a, b) are shown forming an annular ring. As seen in FIG. 5b, two semi-circular UVC lamps (502a, b), which are arranged vertically, may be used at least partially to surround a portion of outlet 406 of a fan assembly 400. Further, as seen in FIG. 5c, two semi-circular UVC lamps (502a, b), arranged horizontally, are shown surrounding a fan assembly 400 (top view of fan assembly).

In both the examples of FIGS. 5b and 5c, air exits the fan assembly 400 and may be directed across the UVC lamp irradiation field for sterilization.

The UVC lamp(s) may include conventional plug-in base and socket arrangements. Thus, the UVC lamp(s) may be inserted and removed from the side of the air sterilization apparatus to facilitate maintenance. For example, when replacing a UVC lamp, disassembly of the apparatus may not be required.

The UVC lamp(s) may be any suitable for the apparatus that are non-ozone producing lamp(s) that produce shortwave ultraviolet energy. For example, a low pressure mercury lamp which generates 85% of its output at a wavelength of 2537 Angstroms may be used. The low pressure mercury lamp is similar to a fluorescent lamp; however, it does not contain fluorescent phosphor. Additionally, the glass envelope of the UVC lamp is transparent to the UVC wavelengths and doped with ozone-suppressing agents. The highest quality glass used for this purpose is made from quartz, such as fused quartz. These differences allow a mercury arc of the lamp to produce predominantly 253.7 nanometers (2537 Angstroms) UV energy unmodified (in conventional fluorescent lamps the phosphor would fluoresce). The use of quartz also minimizes solarization.

As is well known in the art, UVC lamp(s) are also provided with an electrical ballast to limit the amount of current flowing into the electric circuit. The electrical ballast may be configured to control various operating parameters of the UVC lamp. For example, parameters such as, but not limited to, UVC emission strength, turning the UVC lamp on/off, monitoring the number of hours the UVC lamp is illuminated, controlling current of the UV-lamp(s) to maintain constant UVC emission strength based on the number of hours of UVC lamp(s) operation, and emitting a visual signal to indicate that the UVC lamp has expended its useful life span and needs replacement. The UVC lamp may also be remotely controlled.

Figure 6:
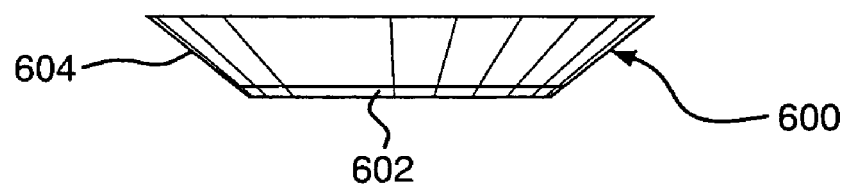
FIG. 6 shows a side view of a baffle of the air sterilization apparatus of FIG. 1.

Turning to FIG. 6, a baffle 600 is shown that can be arranged below the UVC lamp to absorb and direct UV energy. In the instant case, the baffle 600 is comprised of a circular bottom plate 602 with tapered side surfaces 604. These extend toward the UVC lamp near which it is mounted; however, other arrangements may be used. The side surfaces 604 extend circumferentially around the entire periphery of the bottom plate 602.

The baffle 600 may also be adjustable. For example, the baffle may be adjusted vertically by using a threaded rod and fastener arrangement.

If the air sterilization apparatus is located within a room occupied by people, the baffle 600 can prevent occupants of the room from being exposed to UVC energy contained in the UVC irradiation field. UVC energy overexposure can produce transient, painful, acute effects resulting in skin reddening like a sunburn (erythema) and eye irritation (photoconjunctivitis). Both conditions resolve without longer effects within a 24-48 h period if no further exposure occurs. The human skin's protective outer layer (stratum corneum) absorbs ~94% of UVC energy. Indeed the levels of human exposure to naturally occurring, more potent forms of UV from the sun (UVA and UVB) are orders of magnitude higher than levels of UVC provided in the upper room. In accordance with certain embodiments of the present invention, to address concerns, regarding possible human exposure from installed UV systems, the UVC energy produced by the UVC lamp may be shielded with the baffle 600. The baffle 600 may limit or prevent both direct viewing and reflections of the UVC energy from reaching occupants of the room in which the UVC lamp is located. For example, the baffle 600 may limit an occupant's exposure to UVC to below threshold limit values, as are well known in the art. Threshold limit values of UVC eye exposure allow variable levels of exposure as long as a recognized time-weighted average for total exposure is not exceeded during an eight hour period of time.

In accordance with certain embodiments of the present application, the baffle 60 may provide line of sight protection from anywhere in a room at a height of seven to eight feet from the floor. For example, in a room having a ceiling plane of ten feet, direct view of the UVC irradiation field can be at a distance of fifty feet or more. If a room were large enough for viewing at this distance, such exposure would not be likely to cause any damage.

Figure 7:
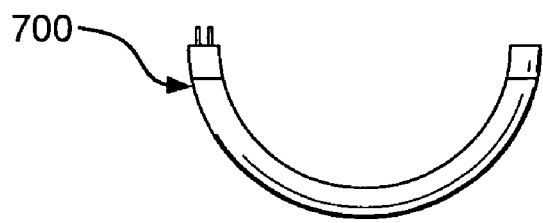
FIG. 7 shows a illuminator lamp of the air sterilization apparatus of FIG. 1.

As seen in FIG. 7, an illuminator lamp 700 may placed below the baffle to illuminate the room in which the air sterilization apparatus is located. Any illuminator lamp 700 may be used, e.g., incandescent, halogen, or neon or xenon bulbs; however, in the examples illustrated in FIGS. 1, 2, and 7, fluorescent lamps are used. Any number of illuminator lamps 700 may be used. Likewise, the fluorescent lamps can be any shape and/or size. The fluorescent lamps may be semi-circular to facilitate insertion and/or removal thereof to facilitate maintenance. The fluorescent lamps use electric current to stimulate mercury atoms, which causes them to release ultraviolet photons. These photons in turn stimulate a phosphor, which emits visible light to illuminate the room. As with the UVC lamp, the fluorescent lamp may be in a plug and socket configuration.

As is well known in the art, a ballast is used for limiting the amount of electrical current flowing into the electrical circuit of the illuminator lamp 700. The illuminator lamp 700 may be remotely controlled.

A control unit may be provided for housing the ballasts of both the UVC lamp and the illuminator lamp, as well as a control for controlling the fan assembly. In addition, all of these components may be controlled remotely and their control functions can be incorporated into single or multiple remote controllers.

Wiring, such as single line feeds, may be run from the control box, ballasts, and/or fan assembly to respective components of the air sterilization apparatus. Electrical components and/or wiring may be insulated with UVC-resistant polytetrafluoroethylene (PTFE).

Figure 8:
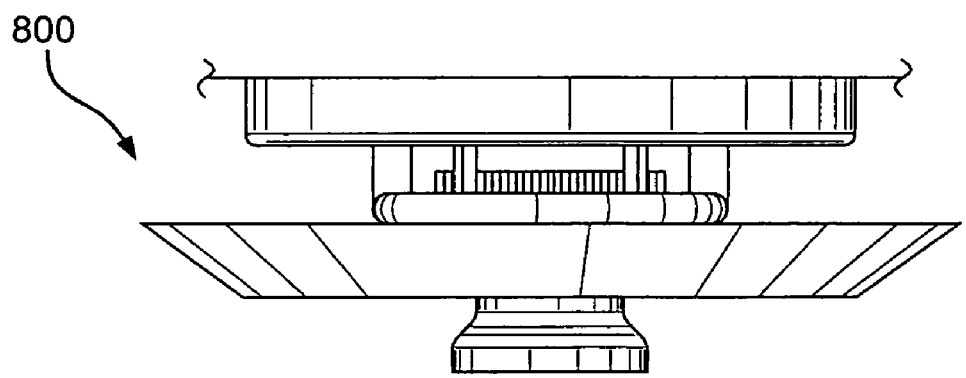
FIG. 8 shows an alternative air sterilization apparatus which may be employed in accordance with certain embodiments of the present invention.

FIG. 8 shows an alternative arrangement for the air sterilization apparatus. This apparatus is identical to that of FIGS. 1-2, explained herein in detail above, except that it does not include an illuminator lamp.

In other embodiments, the air sterilization apparatus may also include a ceiling fan, as is well known in the art.

Figure 9:
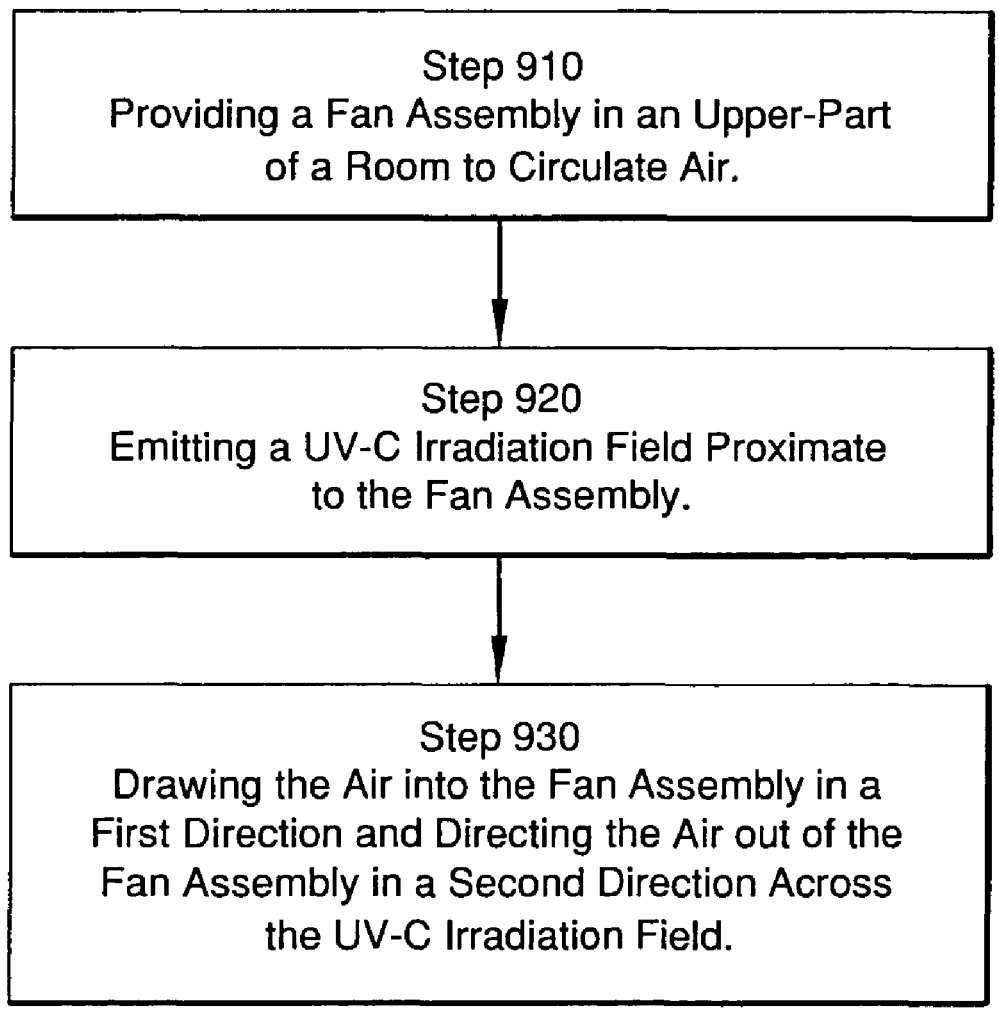
FIG. 9 is a flow chart of method steps that may be employed in accordance with certain embodiments of the present invention.

FIG. 9 shows a flow chart including method steps that may be employed with certain embodiments of the present invention for sterilizing air. Step 910 may include providing a fan assembly in an upper-part of a room to circulate air. Step 920 may include emitting a UVC irradiation field proximate to the fan assembly. Step 930 can include drawing the air into the fan assembly in a first direction and directing the air out of the fan assembly in a second direction across the UVC irradiation field.

In embodiments, not shown, the sequence of method steps may be reordered and steps may be added or removed. The steps may also be modified.

Airborne microorganisms can be detrimental to human and animal health. Potentially harmful airborne microorganisms include viruses, bacteria, fungi, and examples of diseases spread by airborne transmission include tuberculosis, anthrax, measles, influenza, and the threat of ever-more-virulent viruses and the problem of multiple-drug-resistant organisms. Therefore, finding ways to control airborne pathogens and reducing the spread of infectious organisms in indoor environments, such as offices, hospitals, and residences, is increasingly important.

Accordingly, in operation, the air sterilization apparatus discussed hereinabove in detail may be used to sterilize air in buildings, and other enclosed spaces (e.g., hospitals, schools, dormitories, healthcare institutions, offices, homeless shelters, animal confinements, airplanes, etc.), which often contain potentially health threatening bacteria and viruses, particularly so for persons with impaired immune systems. Tuberculosis is an example of an infectious disease that can be contracted by breathing air containing the tuberculosis bacterium. In addition to tuberculosis, other microbial disorders such as influenza, measles, and aerosolized bio-terror agents such as anthrax and smallpox, may be contracted by airborne exposure. To reduce the risk of transmission of disease, the air can be disinfected in various ways, including dilution, filtration, and purification by a UVGI field.

While various embodiments have been described, other embodiments are possible. It should be understood that the foregoing descriptions of various examples of the air sterilization apparatus are not intended to be limiting, and any number of modifications, combinations, and alternatives of the examples may be employed to facilitate sterilization of air.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added to, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A method for sterilizing air, comprising the steps of:
providing an air sterilization apparatus including a baffle, a UVC lamp, and a fan assembly having an inlet and outlet in an upper-part of a room to circulate air;
emitting a UVGI field proximate to the outlet of the fan assembly; and
drawing the air into the fan assembly through the inlet in a first direction and directing the air out through the outlet in a second direction across the UVGI field,
wherein a bottom surface of the UVC lamp is located substantially flush with or above the upper-most surface of the baffle such that horizontal radiation emissions from the UVC lamp are unimpeded by the baffle.

2. The method of claim 1, further comprising:
supporting the fan from the ceiling.

3. The method of claim 1, wherein the first direction is a substantially vertical direction and the second direction is a substantially horizontal direction.

4. The method of claim 1, wherein the air is directed across the upper-part of the room and through the UVGI field.

5. The method of claim 1, wherein the fan assembly pulls air from the lower-part of the room to the upper-part of the room in a substantially vertical direction.

6. The method of claim 1, wherein the air is directed out of the outlet over 360°.

7. The method of claim 1, wherein the air is directed out of the outlet without the use of louvers.

8. The method of claim 1, wherein the air is directed out of the outlet, through the UVGI field, and across the upper-part of the room without the use of louvers.

9. The method of claim 1, wherein the baffle is arranged to limit the UVGI field emission below the baffle.

* * * * *